(12) United States Patent
Ollila et al.

(10) Patent No.: US 10,452,911 B2
(45) Date of Patent: Oct. 22, 2019

(54) GAZE-TRACKING SYSTEM USING CURVED PHOTO-SENSITIVE CHIP

(71) Applicant: Varjo Technologies Oy, Helsinki (FI)

(72) Inventors: Mikko Ollila, Tampere (FI); Klaus Melakari, Oulu (FI); Oiva Arvo Oskari Sahlsten, Salo (FI)

(73) Assignee: VARJO TECHNOLOGIES OY, Helsinki (FI)

( * ) Notice: Subject to any disclaimer, the term of this patent is extended or adjusted under 35 U.S.C. 154(b) by 79 days.

(21) Appl. No.: 15/886,003

(22) Filed: Feb. 1, 2018

(65) Prior Publication Data
US 2019/0236355 A1 Aug. 1, 2019

(51) Int. Cl.
*G06F 3/01* (2006.01)
*G06K 9/00* (2006.01)
*G06K 9/20* (2006.01)

(52) U.S. Cl.
CPC ....... *G06K 9/00604* (2013.01); *G06K 9/2027* (2013.01); *G06K 9/2036* (2013.01)

(58) Field of Classification Search
CPC . G06K 9/00604; G06K 9/2027; G06K 9/2036
USPC ................................................ 348/78
See application file for complete search history.

(56) References Cited

U.S. PATENT DOCUMENTS

2003/0234823 A1* 12/2003 Sato .................. G06F 3/013
715/848
2014/0267848 A1* 9/2014 Wu .................. H04N 9/045
348/277
2016/0321502 A1* 11/2016 Kamath ............. G06Q 30/00
2017/0116476 A1 4/2017 Publicover et al.

FOREIGN PATENT DOCUMENTS

EP     3075315 A1    10/2016

OTHER PUBLICATIONS

The International Search Report and Written Opinion of the international Searching Authority, Application No. PCT/FI2019/050058, dated Mar. 29, 2019, 13 pages.

* cited by examiner

*Primary Examiner* — Patricia I Young
(74) *Attorney, Agent, or Firm* — Ziegler IP Law Group, LLC (57) ABSTRACT

A gaze-tracking system for use in a head-mounted display apparatus, and a method of tracking a user's gaze, via such a gaze-tracking system. The gaze-tracking system includes illuminators for emitting light pulses to illuminate a user's eye; a camera for capturing an image of reflections of the light pulses from the user's eye, the camera including photo-sensitive elements arranged into a chip, wherein a first surface of the chip bulges inwards in a substantially-curved shape, such that a focal plane of photo-sensitive elements positioned proximally to edges of the chip is farther away than a focal plane of photo-sensitive elements positioned substantially at a center portion of the chip, the first surface facing the user's eye; and a processor being configured to control operations of the illuminators and the camera, and to process the captured image to detect a gaze direction of the user.

12 Claims, 5 Drawing Sheets

GAZE-TRACKING SYSTEM USING CURVED PHOTO-SENSITIVE CHIP

TECHNICAL FIELD

The present disclosure relates generally to display apparatuses; and more specifically, to gaze-tracking systems for use in a head-mounted display apparatuses, such gaze-tracking systems comprising illuminators, cameras, and processors. Furthermore, the present disclosure also relates to methods of tracking a user's gaze via the aforementioned gaze-tracking systems.

BACKGROUND

Nowadays, head-mounted display apparatuses (or head-mounted devices) are increasingly being used for a number of purposes such as gaming, education, military training, medicine, and so forth. In such an instance, a simulated environment is presented to a user when he/she wears such a head-mounted display apparatus. The head-mounted display apparatus employs contemporary techniques such as stereoscopy to provide the user with a feeling of complete involvement (namely, immersion) within the simulated environment. Therefore, the simulated environment provides the user with an enhanced perception of reality around him/her. Furthermore, the simulated environment could be a fully virtual environment (namely, virtual reality) as well as a real world environment including virtual objects overlaid thereon (namely, augmented reality).

Lately, gaze-tracking (namely, eye tracking) techniques are being employed to determine a direction of gaze of the user, whilst the user uses the head-mounted display apparatus. Generally, in such gaze-tracking techniques, an illumination source is employed for emitting light towards the user's eyes, and an imaging device (for example, such as a camera) is employed for capturing an image depicting pupils of the user's eyes and reflection(s) of the emitted light from the user's eyes. Consequently, the captured image is employed to determine the gaze direction of the user.

However, there exist limitations associated with implementation of such gaze-tracking techniques. In other words, there exist several optical design constraints associated with equipment for implementing such gaze-tracking techniques. Firstly, the imaging device is required to be arranged outside, or at a peripheral region of the head-mounted display apparatus's field of view. However, for proper imaging, the imaging device needs to be arranged close to the user's eyes, for example, such as a few centimeters away from the user's eyes. In such an instance, the imaging device is required to be arranged within the head-mounted display apparatus, or in frame(s) of the head-mounted display apparatus. Secondly, imaging sensors of the imaging device are limited in their ability to fully focus a convex object such as the user's eye. As a result, there may exist blurriness associated with certain regions of the user's eyes, within the captured image. Consequently, such blurriness severely limits accuracy of the determined gaze direction of the user. Thirdly, a position of the head-mounted display apparatus with respect to the user's eyes is not constant, since the head-mounted display apparatus may move (or get displaced) during use. Therefore, both the equipment for implementing the gaze-tracking techniques, and equipment (for example, such as displays, projectors, and so forth) for rendering images of the simulated environment require precise calibration. Fourthly, if the user wears spectacles whilst using the head-mounted display apparatus, the reflection(s) of the emitted light from the user's eyes gets reflected from lenses of the spectacles. Such reflections need to be recognized and filtered out for determining the gaze direction of the user.

Therefore, in light of the foregoing discussion, there exists a need to overcome the aforementioned drawbacks associated with conventional equipment and techniques for gaze-tracking.

SUMMARY

The present disclosure seeks to provide a gaze-tracking system for use in a head-mounted display apparatus.

The present disclosure also seeks to provide a method of tracking a user's gaze, via a gaze-tracking system of a head-mounted display apparatus.

The present disclosure seeks to provide a solution to the existing problems of optical design constraints and inaccuracies in detected gaze direction, that are associated with conventional equipment for implementing gaze-tracking. An aim of the present disclosure is to provide a solution that overcomes at least partially the problems encountered in the prior art, and to provide robust and efficient gaze-tracking system that accurately determines a gaze direction of a user of the head-mounted display apparatus, whilst not being limited to a particular optical design or arrangement.

In one aspect, an embodiment of the present disclosure provides a gaze-tracking system for use in a head-mounted display apparatus, the gaze-tracking system comprising:

a plurality of illuminators for emitting light pulses to illuminate a user's eye when the head-mounted display apparatus is worn by the user;

at least one camera for capturing an image of reflections of the light pulses from the user's eye, the image being representative of a position of the reflections on an image plane of the at least one camera, the at least one camera comprising a plurality of photo-sensitive elements arranged into at least one chip, wherein a first surface of the at least one chip bulges inwards in a substantially-curved shape, such that a focal plane of photo-sensitive elements positioned proximally to edges of the at least one chip is farther away than a focal plane of photo-sensitive elements positioned substantially at a center portion of the at least one chip, the first surface facing the user's eye when the head-mounted display apparatus is worn by the user; and a processor coupled in communication with the plurality of illuminators and the at least one camera, wherein the processor is configured to control operations of the plurality of illuminators and the at least one camera, and to process the captured image to detect a gaze direction of the user.

In another aspect, an embodiment of the present disclosure provides a method of tracking a user's gaze, via a gaze-tracking system of a head-mounted display apparatus, the gaze-tracking system comprising a plurality of illuminators and at least one camera, the method comprising:

emitting light pulses, via the plurality of illuminators, to illuminate a user's eye when the head-mounted display apparatus is worn by the user;

capturing an image of reflections of the light pulses from the user's eye, via the at least one camera, the image being representative of a position of the reflections on an image plane of the at least one camera, the at least one camera comprising a plurality of photo-sensitive elements arranged into at least one chip, wherein a first surface of the at least one chip bulges inwards in a substantially-curved shape, such that a focal plane of photo-sensitive elements positioned proximally to edges of the at least one chip is farther away than a focal plane of photo-sensitive elements positioned substantially at a center portion of the at least one chip, the first surface facing the user's eye when the head-mounted display apparatus is worn by the user; and processing the captured image to detect a gaze direction of the user.

Embodiments of the present disclosure substantially eliminate or at least partially address the aforementioned problems in the prior art, and enables simple, accurate and efficient tracking of the user's gaze direction.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those in the art will understand that the drawings are not to scale. Wherever possible, like elements have been indicated by identical numbers.

Embodiments of the present disclosure will now be described, by way of example only, with reference to the following diagrams wherein.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practising the present disclosure are also possible.

In one aspect, an embodiment of the present disclosure provides a gaze-tracking system for use in a head-mounted display apparatus, the gaze-tracking system comprising:

a plurality of illuminators for emitting light pulses to illuminate a user's eye when the head-mounted display apparatus is worn by the user;

at least one camera for capturing an image of reflections of the light pulses from the user's eye, the image being representative of a position of the reflections on an image plane of the at least one camera, the at least one camera comprising a plurality of photo-sensitive elements arranged into at least one chip, wherein a first surface of the at least one chip bulges inwards in a substantially-curved shape, such that a focal plane of photo-sensitive elements positioned proximally to edges of the at least one chip is farther away than a focal plane of photo-sensitive elements positioned substantially at a center portion of the at least one chip, the first surface facing the user's eye when the head-mounted display apparatus is worn by the user; and a processor coupled in communication with the plurality of illuminators and the at least one camera, wherein the processor is configured to control operations of the plurality of illuminators and the at least one camera, and to process the captured image to detect a gaze direction of the user.

In another aspect, an embodiment of the present disclosure provides a method of tracking a user's gaze, via a gaze-tracking system of a head-mounted display apparatus, the gaze-tracking system comprising a plurality of illuminators and at least one camera, the method comprising:

emitting light pulses, via the plurality of illuminators, to illuminate a user's eye when the head-mounted display apparatus is worn by the user;

capturing an image of reflections of the light pulses from the user's eye, via the at least one camera, the image being representative of a position of the reflections on an image plane of the at least one camera, the at least one camera comprising a plurality of photo-sensitive elements arranged into at least one chip, wherein a first surface of the at least one chip bulges inwards in a substantially-curved shape, such that a focal plane of photo-sensitive elements positioned proximally to edges of the at least one chip is farther away than a focal plane of photo-sensitive elements positioned substantially at a center portion of the at least one chip, the first surface facing the user's eye when the head-mounted display apparatus is worn by the user; and processing the captured image to detect a gaze direction of the user.

The present disclosure provides the aforementioned gaze-tracking system and the aforementioned method. The gaze-tracking system is not limited to a particular optical design or arrangement, thereby, allowing for components of the gaze-tracking system to be arranged in any suitable manner. Furthermore, owing to the substantially curved shape of the at least one chip having the plurality of photo-sensitive elements arranged therein, the at least one camera of the gaze-tracking system allows for fully focusing the user's eye. Therefore, the captured image is substantially free from blurriness, and accurately represents the position of the reflections of the emitted light pulses. Moreover, the described gaze-tracking system accurately detects the gaze direction of the user, even upon movement of the head-mounted display apparatus with respect to the user's eye. Additionally, such a gaze-tracking system could be employed for users wearing spectacles, by optically filtering unwanted reflections of the light pulses. Beneficially, the gaze-tracking system is robust and reliable, while the described method allows for highly accurate determination of the gaze direction of the user, in a simple, efficient manner.

Throughout the present disclosure, the term "head-mounted display apparatus" relates to specialized equipment that is configured to present a simulated environment to a user when the head-mounted display apparatus is worn by the user on his/her head. In such an instance, the head-mounted display apparatus is operable to act as a device (for example, such as a virtual reality headset, an augmented reality headset, a pair of virtual reality glasses, a pair of augmented reality glasses, and so forth) for presenting a visual scene of the simulated environment to the user.

Throughout the present disclosure, the term "gaze-tracking system" relates to specialized equipment for detecting a direction of gaze (namely, the gaze direction) of the user. The head-mounted display apparatus uses the gaze-tracking system for determining aforesaid gaze direction via non-invasive techniques. Beneficially, an accurate detection of the gaze direction facilitates the head-mounted display apparatus to closely implement gaze contingency thereon. As an example, the gaze-tracking system may be employed to detect the gaze direction of the user's eye for projecting (i) a region of a visual scene whereat the user's gaze is focused, on and around the fovea of the user's eye, and (ii) a remaining region of the visual scene on the retina of the user's eye, of which the fovea is just a small part. Therefore, even upon a change in the gaze direction (namely, due to a movement of the user's eye), active foveation is implemented within the head-mounted display apparatus.

It is to be understood that the gaze-tracking system may also be referred to as an "eye-tracker system", a "means for detecting a gaze direction", a "means for tracking a gaze direction", or a "gaze-tracking unit".

Throughout the present disclosure, the term "plurality of illuminators" relates to light sources configured to emit light pulses for illuminating the user's eye. In such a case, the emitted light pulses illuminate at least one of: the pupil of the user's eye, the iris of the user's eye, the sclera of the user's eye. Optionally, the plurality of illuminators could emit the light pulses periodically or intermittently. Alternatively, optionally, the plurality of illuminators emit light continuously. It will be appreciated that the light pulses emitted by the plurality of illuminators are reflected from an outer surface (for example, such as cornea) of the user's eye, thereby constituting corneal reflections (namely, glints) in the user's eye.

Optionally, the light pulses emitted by the plurality of illuminators have an infra-red wavelength or a near infra-red wavelength. The light pulses of infrared or near-infrared wavelength are invisible to the human eye, thereby, reducing unwanted distraction when such light pulses are incident upon the user's eye. Alternatively, optionally, the light pulses emitted by the plurality of illuminators have a visible wavelength.

Optionally, the plurality of illuminators are implemented by way of at least one of: active light sources, passive light sources. Throughout the present disclosure, the term "active light sources" relates to equipment that directly emits light therefrom whereas the term "passive light sources" relates to equipment that employs light emanating from an active light source, to emit light therefrom. It will be appreciated that the passive light sources could (i) direct the light emitted by the active light source towards the user's eye and/or (ii) absorb the light emitted by the active light source and consequently emit light of a different wavelength towards the user's eye. Optionally, the passive light sources are at least one of: fluorescent light sources, phosphorescent light sources. In an example, the plurality of illuminators are implemented by way of two infrared light-emitting diodes. In another example, the plurality of illuminators are implemented by way of two infrared light-emitting diodes and one fluorescent light source that absorbs visible light emitted by a Light Emitting Diode (LED)-based display and emits infrared light therefrom.

Furthermore, optionally, the plurality of illuminators are implemented by way of at least one of: infrared light-emitting diodes, infrared lasers, infrared light projectors, infrared light-emitting diode based displays, visible light-emitting diodes, visible light lasers, visible light projectors, infrared light-emitting diode based displays, fluorescent lamps, fluorescent displays, fluorescent projectors, phosphorescent lamps, phosphorescent displays, phosphorescent projectors.

Optionally, the plurality of illuminators, either alone or in combination with at least one first optical element, are operable to produce structured light pulses to illuminate the user's eye. Optionally, in this regard, the plurality of illuminators are arranged substantially proximal to at least one objective lens of the at least one camera. As a result, a focal distance of the at least one objective lens is substantially equal to a sum of the distance between the plurality of illuminators and the surface of the user's eye and a distance between the at least one objective lens and the surface of the user's eye. It will be appreciated that such an arrangement of the plurality of illuminators and the at least one objective lens allows for capturing an acceptably sharp image of reflections of the structured light pulses from the user's eye. Examples of the at least one first optical element include, but are not limited to, a freeform mirror, a freeform lens, a freeform prism, a light guide.

In an example implementation, when the plurality of illuminators are implemented by way of the infrared light-emitting diodes or the visible light-emitting diodes, the focal distance of the at least one objective lens may be substantially equal to the sum of the distance between the plurality of illuminators and the surface of the user's eye and the distance between the at least one objective lens and the surface of the user's eye.

In another example implementation, when the plurality of illuminators are implemented by way of the infrared lasers or the visible light lasers, the focal distance of the at least one objective lens may be substantially equal to the distance between the at least one objective lens and the surface of the user's eye.

Optionally, in operation, the plurality of illuminators directly emit the light pulses onto the user's eye.

Alternatively, optionally, the plurality of illuminators are operable to emit the light pulses in a direction that is at a predefined angle to a view direction of the user's eye, and wherein the gaze-tracking system further comprises at least one substantially-reflective optical element for reflecting the light emitted by the plurality of illuminators towards the user's eye. In such a case, the at least one substantially-reflective optical element is positioned on an optical path of the emitted light pulses, namely between the plurality of illuminators and the user's eye. As an example, the light can be emitted by the plurality of illuminators in a direction that is substantially perpendicular to the view direction of the user's eye. Optionally, the at least one substantially-reflective optical element is implemented by way of at least one of: a semi-transparent mirror, a fully reflective mirror, a semi-transparent reflector, a prism, a polarizer. As an example, the semi-transparent mirror for implementing the optical element may be a pellicle mirror.

More optionally, the predefined angle may be selected so as to reduce a size of the gaze-tracking system. In an embodiment, the predefined angle ranges from 120 degrees to 240 degrees. In such an instance, the predefined angle may be, for example, such as 120, 130, 140, 150, 160, 170, 180, 190, 200, 210, 220, 230, or 240 degrees with respect to a view direction of the user's eye. In another embodiment, the predefined angle is lesser than 120 degrees (for example, such as 90, 95, 100, 105, 110, or 115 degrees) or greater than 240 degrees (for example, such as 245, 250, 255, 260, 265, or 270 degrees) with respect to the view direction of the user's eye.

It will be appreciated that the plurality of illuminators are optionally arranged for illuminating the user's eye so as to facilitate both bright-pupil tracking and dark-pupil tracking. Furthermore, for implementing the bright-pupil tracking, the light pulses emitted by the plurality of illuminators are arranged to be incident upon the user's eye substantially along the view direction of the user's eye. Moreover, for implementing the dark-pupil tracking, the light pulses emitted by the plurality of illuminators are arranged to be incident upon the user's eye substantially away from (namely, offset from) the view direction of the user's eye.

Optionally, the plurality of illuminators comprise at least a first illuminator and a second illuminator that are to be arranged in a manner that light pulses emitted by the first illuminator are incident upon a first portion of the user's eye, and light pulses emitted by the second illuminator are incident upon a second portion of the user's eye, the first portion of the user's eye being farther away from the at least one camera than the second portion of the user's eye, wherein the first and second portions lie within a depth of field (or depth of focus) of a focal plane of the at least one camera. It is to be understood that depth of field of a given focal plane relates to a region around the given focal plane within which if light is made incident, a reflection of the light appears acceptably sharp when focused onto the image plane of the at least one camera. This may be attributed to the fact that a reduction in focus of the at least one camera with increase in distance from the given focal plane, is very gradual. Therefore, when the light is incident within the depth of field of the given focal plane, a reduction in sharpness (namely, focus) is imperceptible whilst imaging the reflection of the light.

Therefore, it will be appreciated that the aforesaid arrangement allows for the reflections of the light pulses emitted by the first and second illuminators to appear acceptably sharp when they are focused onto the image plane of the at least one camera.

Optionally, the focal plane of the at least one camera is associated with a near-field depth of field and a far-field depth of field, wherein the near-field depth of field is substantially lesser than the far-field depth of field. The near-field depth of field relates to depth of field corresponding to a region of the focal plane that lies substantially along a camera optical axis of the at least one camera. Furthermore, the far-field depth of field relates to depth of field corresponding to regions of the focal plane that lie substantially away from the camera optical axis of the at least one camera. Such near-field and far-field depth of fields have been shown in conjunction with FIG. 2, as elucidated in detail below. Furthermore, the near-field and far-field depth of fields may substantially correspond to a circle of confusion within the captured image of the reflections of the light pulses. As an example, such a circle of confusion may have a radius of 2 pixels from a given pixel representing a given focus point.

Optionally, the near-field depth of field substantially corresponds to a proximal region of the focal plane of the at least one camera, wherein a position of the focal plane of the at least one camera substantially corresponds to a position of the user's eye.

In an example, when the structured light pulses are produced to illuminate the user's eye, such structured light pulses may be made incident upon a surface of the user's eye that lies within the near-field depth of field.

In another example, when divergent light pulses are produced to illuminate the user's eye, such divergent light pulses may be made incident upon a surface of the user's eye that lies within the far-field depth of field. Furthermore, in such an example, the far-field depth of field may extend upto positions of the plurality of illuminators.

Optionally, the gaze-tracking system comprises at least one axicon lens, wherein optical characteristics and/or an arrangement of the at least one axicon lens allow for extending the depth of field of the focal plane of the at least one camera. The at least one axicon lens could have a symmetric shape or an asymmetric shape. Furthermore, the at least one axicon lens is arranged substantially along the camera optical axis of the at least one camera, between the at least one objective lens and at least one imaging sensor of the at least one camera. It will be appreciated that an extended depth of field allows for capturing a greater portion of the image of reflections with acceptable sharpness as compared to a relatively smaller depth of field.

Optionally, the light pulses emitted by the first and second illuminators have same wavelength. Alternatively, optionally, the light pulses emitted by the first and second illuminators have different wavelengths, a first wavelength of the light pulses emitted by the first illuminator being longer than a second wavelength of the light pulses emitted by the second illuminator.

Optionally, the plurality of illuminators further comprise a third illuminator that is to be arranged in a manner that light pulses emitted by the third illuminator are employed to illuminate the user's eye for enabling detection of a position of the pupil of the user's eye. Optionally, in this regard, a third wavelength of the light pulses emitted by the third illuminator is shorter than the first wavelength, but longer than the second wavelength.

As mentioned previously, the at least one camera captures the image of reflections of the light pulses from the user's eye. The image is representative of a position of the reflections on an image plane of the at least one camera. In such an instance, the image depicts positions and/or arrangement (namely, intergeometry) of reflections of the light pulses emitted by the plurality of illuminators. In other words, the image depicts the positions and/or arrangement of the glints in the user's eye. Throughout the present disclosure, the term "image plane of the at least one camera" relates to a region of the camera whereat the reflections of the light pulses are focused onto the plurality of photo-sensitive elements, to create the aforesaid image. In other words, the image plane of the at least one camera is an imaging surface of the at least one camera, and lies within the at least one camera.

Optionally, when the plurality of illuminators produce the structured light pulses, the reflections of the structured light pulses appear as a plurality of glints in the captured image. Optionally, the plurality of glints are in a form of substantially V-shaped characters.

Optionally, the gaze-tracking system comprises at least one camera per eye of the user. Optionally, accurate gaze-tracking can be done by employing a single camera for both eyes of the user, since both eyes of the user often move synchronously.

Optionally, the at least one camera is arranged substantially along the gaze direction of the user's eye. In other words, the at least one camera is arranged to capture a front perspective view of the reflections of the light pulses from the user's eye. In such an instance, none or minimal perspective correction is required whilst processing the captured image of the reflections of the light pulses. Furthermore, such an arrangement of the at least one camera with respect to the user's eye is hereinafter referred to as the "frontal imaging arrangement".

Alternatively, optionally, the at least one camera is arranged substantially away from the gaze direction of the user's eye. In other words, the at least one camera is arranged to capture a side perspective view of the reflections of the light pulses from the user's eye. In such an instance, significant perspective correction is required whilst processing the captured image of the reflections of the light pulses. Furthermore, such an arrangement of the at least one camera with respect to the user's eye is hereinafter referred to as the "side imaging arrangement".

Optionally, in the side imaging arrangement, the gaze-tracking system further comprises at least one second optical element that is arranged for directing the reflections of the light pulses from the user's eye towards the at least one camera. In such a case, the at least one second optical element is positioned on an optical path of the reflected light pulses, namely between the user's eye and the at least one camera. As an example, the at least one camera may be arranged substantially perpendicular to the view direction of the user's eye. Therefore, the at least one second optical element may direct (namely, guide or reflect) the reflections of the light pulses towards the at least one camera.

Optionally, the at least one second optical element is implemented by way of at least one of: a semi-transparent mirror, a semi-transparent film, a prism, a beam splitter, a polarizer, an optical waveguide.

Optionally, the head-mounted display apparatus comprises the at least one second optical element.

The at least one camera comprises the plurality of photo-sensitive elements arranged into the at least one chip. In such an instance, the plurality of photo-sensitive elements are configured to detect and process the reflections of light pulses to capture the aforesaid image. It will be appreciated that the plurality of photo-sensitive elements are operable to act as the at least one imaging sensor of the at least one camera and the at least one chip is operable to act as the image plane of the at least one camera. Furthermore, optionally, the plurality of photo-sensitive elements of the at least one chip are arranged in a grid-like manner. As an example, the at least one camera comprises 256 photo-sensitive elements arranged into a single chip as a 16*16 grid. Optionally, one photo-sensitive element corresponds to one pixel of the image captured by the at least one camera. Examples of the plurality of photo-sensitive elements include, but are not limited to, photodiodes, photoresistors, phototransistors, and photosensitive field effect transistors.

In an embodiment, the at least one chip is polygonal in shape. In another embodiment, the at least one chip is elliptical in shape. In another embodiment, the at least one chip is circular in shape. In yet another embodiment, the at least one chip is freeform in shape.

Furthermore, the first surface of the at least one chip bulges inwards in a substantially-curved shape, such that the focal plane of photo-sensitive elements positioned proximally to edges of the at least one chip is farther away than the focal plane of photo-sensitive elements positioned substantially at the center portion of the at least one chip, the first surface facing the user's eye when the head-mounted display apparatus is worn by the user. Therefore, in such an instance, the at least one chip appears to be concave (namely, curved inwards) with respect to the user's eye. It is to be understood that a given focal plane corresponding to a given photo-sensitive element relates to an imaginary two-dimensional plane in front of a given camera comprising the given photo-sensitive element, wherein the given focal plane passes through a focal point corresponding to the given photo-sensitive element. In other words, a reflection of light that is incident upon the given focal plane, would be focused with maximum sharpness at the given photo-sensitive element. Furthermore, optionally, the given focal plane is oriented substantially parallel to the given photo-sensitive element and substantially perpendicular to an optical axis of the given camera.

Therefore, it will be appreciated that photo-sensitive elements positioned proximally to edges of the at least one chip could be employed to sharply focus light incident at larger distances from (namely, farther to) the at least one chip whereas the photo-sensitive elements positioned substantially at the center portion of the at least one chip could be employed to sharply focus light incident at smaller distances from (namely, closer to) the at least one chip. Furthermore, it will be appreciated that owing to the aforesaid shape of the at least one chip, there would be a plurality of focal planes corresponding to the plurality of photo-sensitive elements. Therefore, the focal plane of the at least one camera is a resultant of such plurality of focal planes, and is substantially-curved in shape. In an example, the focal plane of the at least one camera may be substantially-curved in a manner that the focal plane bulges outward towards the first surface of the at least one chip. Notably, the focal plane of the at least one camera will no longer be a two-dimensional plane, and would rather be a three-dimensional surface. Beneficially, such a curved focal plane of the at least one camera allows for accurately focusing convex objects (for example, such as the user's eye). One such focal plane of the at least one camera has been shown in conjunction with FIG. 2, as elucidated in detail below.

It will be appreciated that use of the at least one substantially-curved chip allows for simplifying design of the at least one objective lens of the at least one camera. It will be appreciated that a design of an objective lens corresponding to a substantially-curved imaging sensor is much simpler than a design of an objective lens corresponding to a substantially-flat imaging sensor. Notably, the substantially-flat imaging sensor requires the objective lens to include an additional aspheric element for reducing spherical and chromatic aberrations within the gaze-tracking system whereas the substantially-curved imaging sensor allows for reducing spherical and chromatic aberrations owing to its curved design. Therefore, use of the substantially-curved imaging sensor minimizes optical design constraints associated with the at least one objective lens of the at least one camera.

Optionally, the at least one chip is attached to a substantially-concave surface. In such an instance, the aforesaid attachment allows for maintaining the aforesaid substantially-curved shape of the at least one chip, in order to provide the substantially-curved focal plane of the at least one camera. Optionally, the at least one chip could be attached to the substantially-concave surface by way of at least one of: adhesive, screws, clamps, rivets.

Optionally, the at least one chip has a substantially-flat shape. Optionally, in this regard, the at least one chip is flexible (namely, pliable) so as to be attached to the substantially-concave surface. Therefore, such an arrangement allows for arranging the at least one chip in a substantially-curved shape, to provide the substantially-curved focal plane of the at least one camera.

Alternatively, optionally, when the at least one chip has the substantially-flat shape, the at least one chip is substantially-inflexible (namely, rigid).

In the frontal imaging arrangement, the at least one chip is arranged substantially perpendicularly to the camera optical axis of the at least one camera. In the side imaging arrangement, the at least one chip is optionally tilted with respect to the camera optical axis of the at least one camera.

As mentioned previously, the first surface of the at least one chip faces the user's eye when the head-mounted display apparatus is worn by the user. Optionally, the at least one chip is arranged in a manner that the center portion of the at least one chip lies substantially along an optical axis of the user's eye. In such a case, the at least one camera and the user's eye are substantially coaxial. In other words, the optical axis of the user's eye and the camera optical axis of the at least one camera are same. Such an arrangement is employed to implement the frontal imaging arrangement. Alternatively, optionally, the at least one chip is arranged in a manner that the optical axis of the user's eye is oblique (namely, tilted) with respect to the camera optical axis of the at least one camera. Such an arrangement is employed to implement the side imaging arrangement.

Optionally, the gaze-tracking system further comprises at least one third optical element that is configured to adjust an optical alignment between the focal plane of the at least one camera, the at least one objective lens and the image plane of the at least one camera. Optionally, in this regard, the at least one third optical element is arranged on the optical path of the reflections of the light pulses, namely between the at least one objective lens and the at least one chip of the at least one camera. The at least one third optical element has optical characteristics and/or is arranged in a manner that the reflections of light pulses which are incident upon the focal plane, are well-focused at the image plane, even upon change in orientation of the at least one objective lens. The at least one third optical element could have a symmetric shape or an asymmetric shape. Optionally, the at least one third optical element is implemented by way of at least one of: a field flattener lens, a plano-concave lens, a prism. It will be appreciated that a strong field lens allows for reducing the size of the at least one chip.

In one example implementation, the at least one third optical element (for example, such as the field flattener lens) is employed in an instance when the at least one objective lens is tilted with respect to the camera optical axis of the at least one camera (for example, in the side imaging arrangement).

In another example implementation, the at least one third optical element (for example, such as the plano-concave field lens) is employed in an instance when the at least one chip is substantially-flat shaped, and arranged substantially perpendicularly to the camera optical axis of the at least one camera (for example, in the frontal imaging arrangement).

In yet another example implementation, the at least one third optical element (for example, such as the prism) is arranged between the at least one objective lens and the at least one chip, in the side imaging arrangement. Such a prism could also direct the reflections of the light pulses onto the at least one chip in a manner so as to implement optical perspective correction that is required for the side imaging arrangement.

Optionally, the at least one camera comprises at least one optical filter for blocking unwanted parts of light spectrum, the at least one optical filter being positioned on an optical path of the reflections. More optionally, one optical filter is implemented per photo-sensitive element of the at least one camera. In such an instance, the at least one optical filter is implemented in a manner that one optical filter is superposed on one photo-sensitive element. Therefore, the at least one optical filter is operable to filter the reflections of light pulses from the user's eye, prior to incidence of such reflections onto the plurality of photo-sensitive elements. Optionally, the at least one optical filter is implemented by way at least one bandpass filter, wherein one bandpass filter is configured to pass therethrough, only light within a specific wavelength range. Consequently, such filtered light is incident upon the plurality of photo-sensitive elements. In such an instance, the specific wavelength range could be selected as per requirement. In an example, the at least one optical filter may be implemented by way of a bandpass filter that is configured to pass therethrough, only reflections of the light pulses within a wavelength range of 800 nanometer to 950 nanometer. In another example, the at least one optical filter may be implemented by way of a plurality of bandpass filters that are configured to pass therethrough, only reflections of the light pulses within a wavelength range of 380 nanometer to 760 nanometer. In such an instance, a rich coloured image indicative of spectral properties of the reflections of the light pulses, is captured by the at least one camera.

In an embodiment, the plurality of photo-sensitive elements and the at least one optical filter are implemented together within the at least one camera. In another embodiment, the plurality of photo-sensitive elements and the at least one optical filter are implemented separately within the at least one camera. In yet another embodiment, the plurality of photo-sensitive elements are implemented within the at least one camera whereas the at least one optical filter is implemented external to the at least one camera.

Optionally, the at least one camera is implemented by at least one of: a digital camera, a hyperspectral camera, an RGB-D camera, a Light Detection and Ranging (LiDAR) camera, a Time-of-Flight (ToF) camera, a laser rangefinder, a stereo camera, a plenoptic camera, an infrared camera Optionally, the gaze-tracking system further comprises at least one optical element positioned on an optical path of the reflections, wherein optical characteristics and/or an arrangement of the at least one optical element are such that a shift in a given portion of the at least one chip along the camera optical axis by a micrometer leads to a shift in a focal plane of photo-sensitive elements positioned within the given portion of the at least one chip along the camera optical axis by a certain distance, the certain distance lying within a range of 1 mm to 10 mm. In such an instance, the reflections of the light pulses substantially pass through the at least one optical element to be incident upon the image plane of the at least one camera. Notably, the shift in the given portion of the at least one chip along the camera optical axis could be implemented by way of at least one of: changing a curvature of the at least one chip, moving the at least one chip along the camera optical axis. It will be appreciated that the optical properties (for example, such as transmittance-reflectance properties, refractive index, and so forth) and/or the arrangement of the at least one optical element allow for such a miniscule shift in the given portion of the at least one chip along the camera optical axis, to consequently shift the focal plane of photo-sensitive elements positioned within the given portion of the at least one chip along the camera optical axis by a relatively substantial distance.

Optionally, the at least one optical element is implemented by way of at least one of: a lens, a semi-transparent mirror, a semi-transparent film, a prism, a field lens, a polarizer, an optical waveguide.

As mentioned previously, the processor is configured to control operations of the plurality of illuminators and the at least one camera, and to process the captured image to detect a gaze direction of the user. The processor could be hardware, software, firmware or a combination of these, suitable for implementing the aforesaid functionality. Optionally, the processor processes the image by employing at least one image processing algorithm. The at least one image processing algorithm is employed to detect the pupil of the user's eye and the positions and/or arrangement of the reflections of the light pulses in the user's eye. Therefore, the at least one image processing algorithm is employed to analyze a relationship between the position of the pupil of the user's eye and the reflections of the light, to accurately detect the gaze direction of the user. Optionally, the processor employs information pertaining to an arrangement of the plurality of illuminators, for detecting the gaze direction of the user. In such an instance, positions of the plurality of illuminators with respect to the eye, and the positions of the reflections of the light pulses emitted therefrom, facilitate accurate detection of the gaze direction of the user.

The present disclosure also relates to the method as described above. Various embodiments and variants disclosed above apply mutatis mutandis to the method.

Optionally, in the method, the plurality of illuminators comprise at least the first illuminator and the second illuminator, and the method further comprises arranging the first illuminator and the second illuminator in a manner that light pulses emitted by the first illuminator are incident upon the first portion of the user's eye, and light pulses emitted by the second illuminator are incident upon the second portion of the user's eye, the first portion of the user's eye being farther away from the at least one camera than the second portion of the user's eye, wherein the first and second portions lie within the depth of field of the focal plane of the at least one camera. Optionally, in the method, the gaze-tracking system further comprises at least one optical element positioned on an optical path of the reflections, wherein optical characteristics and/or an arrangement of the at least one optical element are such that a shift in a given portion of the at least one chip along a camera optical axis by a micrometer leads to a shift in a focal plane of photo-sensitive elements positioned within the given portion of the at least one chip along the camera optical axis by a certain distance, the certain distance lying within a range of 1 mm to 10 mm. Optionally, in the method, the at least one chip is attached to a substantially-concave surface. Optionally, in the method, the light pulses emitted by the plurality of illuminators have an infra-red wavelength or a near infra-red wavelength. Optionally, in the method, the at least one camera comprises the at least one optical filter for blocking unwanted parts of light spectrum, the at least one optical filter being positioned on an optical path of the reflections.

DETAILED DESCRIPTION OF THE DRAWINGS

Figure 1:
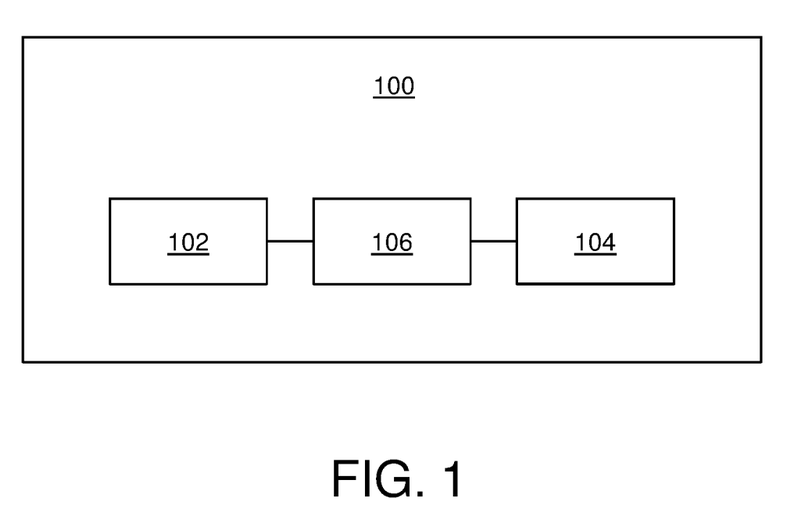
FIG. 1 illustrates a block diagram of a gaze-tracking system for use in a head-mounted display apparatus, in accordance with an embodiment of the present disclosure.

Referring to FIG. 1, illustrated is a block diagram of a gaze-tracking system 100 for use in a head-mounted display apparatus (not shown), in accordance with an embodiment of the present disclosure. The gaze-tracking system 100 comprises a plurality of illuminators 102 for emitting light pulses to illuminate a user's eye when the head-mounted display apparatus is worn by the user, at least one camera 104 for capturing an image of reflections of the light pulses from the user's eye; and a processor 106 coupled in communication with the plurality of illuminators 102 and the at least one camera 104. The image captured by the at least one camera 104 is representative of a position of the reflections on an image plane of the at least one camera 104. The at least one camera 104 comprises a plurality of photo-sensitive elements (not shown) arranged into at least one chip (not shown). The processor 106 is configured to control operations of the plurality of illuminators 102 and the at least one camera 104, and to process the captured image to detect a gaze direction of the user.

Figure 2:
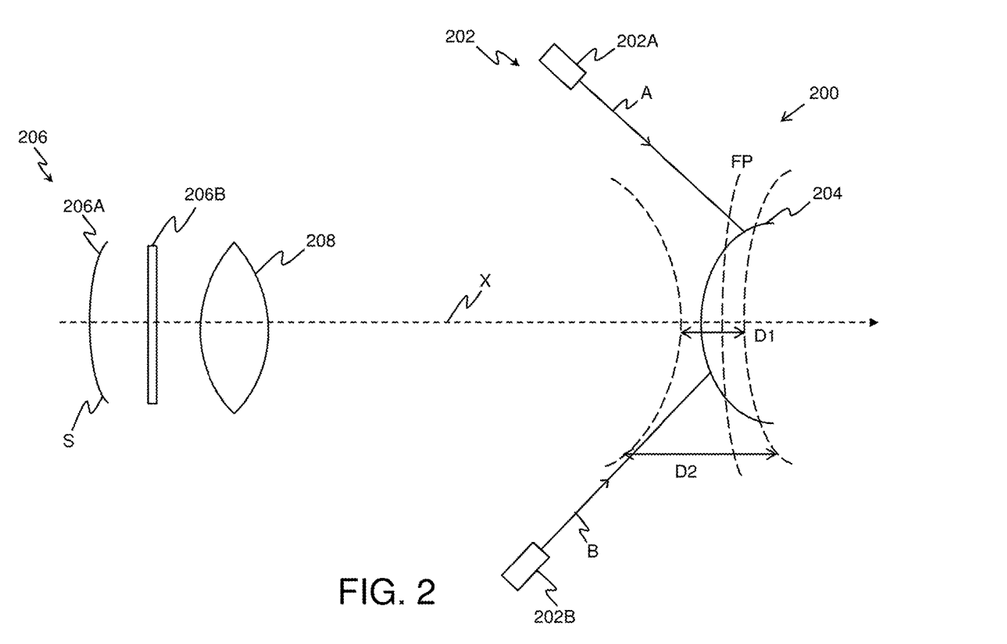
FIG. 2 illustrates an exemplary implementation of the gaze-tracking system, in accordance with an embodiment of the present disclosure.

Referring to FIG. 2, illustrated is an exemplary implementation of a gaze-tracking system 200, in accordance with an embodiment of the present disclosure. As shown, the gaze-tracking system 200 comprises a plurality of illuminators 202 for emitting light pulses to illuminate a user's eye 204 when a head-mounted display apparatus (not shown) is worn by the user. As shown, the plurality of illuminators 202 optionally comprise at least a first illuminator 202A and a second illuminator 202B. As shown, ray A depicts light emitted by the first illuminator 202A and ray B depicts light emitted by the second illuminator 202B.

Furthermore, the gaze-tracking system 200 comprises at least one camera 206 for capturing an image of reflections of the light pulses from the user's eye 204, the image being representative of a position of the reflections on an image plane of the at least one camera 206. The at least one camera 206 comprises a plurality of photo-sensitive elements arranged into at least one chip 206A, wherein a first surface S of the at least one chip 206A bulges inwards in a substantially-curved shape, such that a focal plane of photo-sensitive elements positioned proximally to edges of the at least one chip 206A is farther away than a focal plane of photo-sensitive elements positioned substantially at a center portion of the at least one chip 206A. The first surface S faces the user's eye 204 when the head-mounted display apparatus is worn by the user. Moreover, optionally, the at least one camera 206 comprises at least one optical filter, depicted as an optical filter 206B for blocking unwanted parts of light spectrum, the at least one optical filter 206B being positioned on an optical path of the reflections.

In the gaze-tracking system 200, the first illuminator 202A and the second illuminator 202B are arranged in a manner that light pulses emitted by the first illuminator 202A are incident upon a first portion of the user's eye 204, and light pulses emitted by the second illuminator 202B are incident upon a second portion of the user's eye 204, the first portion of the user's eye 204 being farther away from the at least one camera 206 than the second portion of the user's eye 204, wherein the first and second portions lie within a depth of field of a focal plane FP of the at least one camera 206. As shown, the focal plane FP is associated with a near-field depth of field D1 and a far-field depth of field D2, wherein the near-field depth of field D1 is substantially lesser than the far-field depth of field D2. Notably, limits of the aforesaid near-field and far-field depth of fields D1 and D2 are depicted as dashed lines.

Moreover, the gaze-tracking system 200 comprises a processor (not shown) coupled in communication with the plurality of illuminators 202 and the at least one camera 206. As shown, the gaze-tracking system 200 optionally comprises at least one optical element, depicted as a lens 208 positioned on an optical path of the reflections, wherein optical characteristics and/or an arrangement of the at least one optical element 208 are such that a shift in a given portion of the at least one chip 206A along a camera optical axis X by a micrometer leads to a shift in a focal plane of photo-sensitive elements positioned within the given portion of the at least one chip 206A along the camera optical axis X by a certain distance, the certain distance lying within a range of 1 mm to 10 mm.

It is to be understood by a person skilled in the art that the FIG. 2 includes simplified arrangement for implementation of the gaze-tracking system 200 for sake of clarity only, which should not unduly limit the scope of the claims herein. The person skilled in the art will recognize many variations, alternatives, and modifications of embodiments of the present disclosure.

Referring to FIGS. 3A, 3B, 3C, 3D, 3E, 3F and 3G, illustrated are exemplary implementations of frontal imaging arrangements (notably, FIGS. 3A, 3B and 3C) and side imaging arrangements (notably, FIGS. 3D, 3E, 3F and 3G) of a gaze-tracking system 300, in accordance with different embodiments of the present disclosure. It may be understood by a person skilled in the art that FIGS. 3A-3G include simplified arrangements for the implementation of the frontal and side imaging arrangements for the sake of clarity only, which should not unduly limit the scope of the claims herein. The person skilled in the art will recognize many variations, alternatives, and modifications of embodiments of the present disclosure.

Figure 3A:
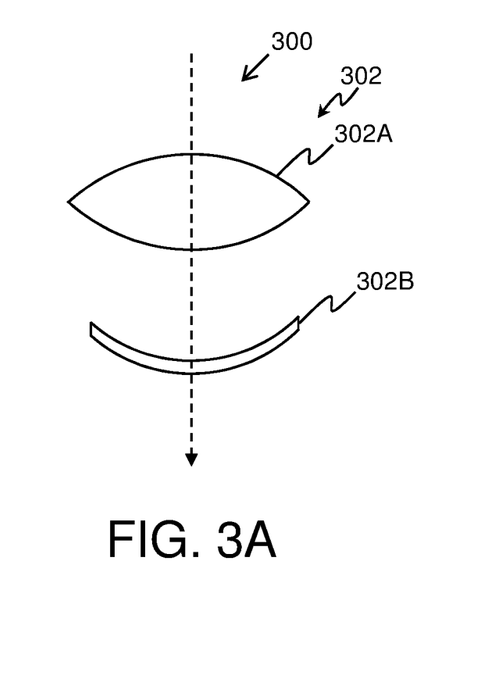
FIGS. 3A, 3B and 3C illustrate exemplary implementations of a frontal imaging arrangement of a gaze-tracking system, in accordance with different embodiments of the present disclosure.
Figure 3B:
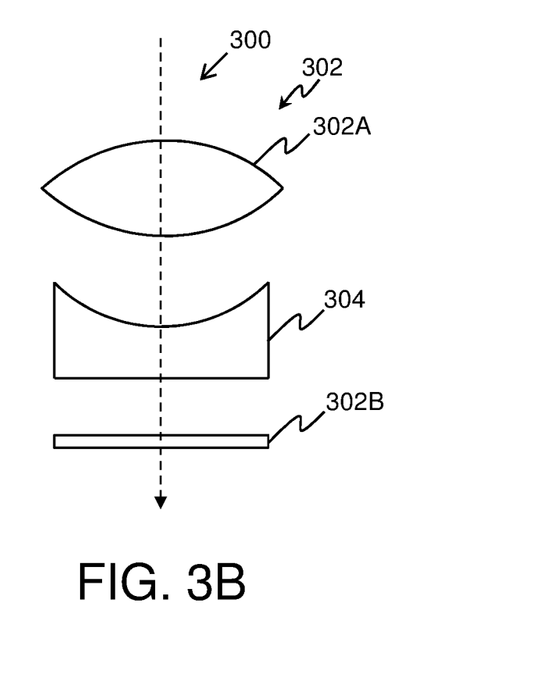
Figure 3C:
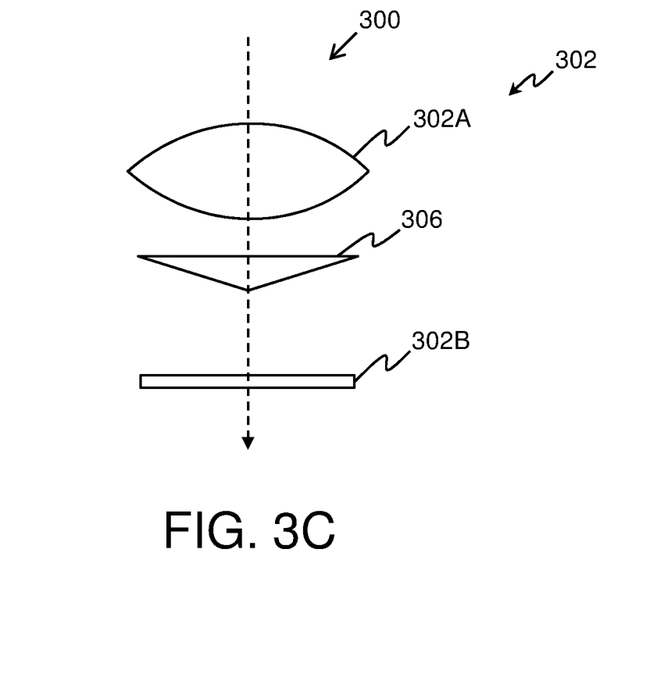

In FIGS. 3A-3G, a direction of gaze of a user's eye (not shown) is depicted by way of the dashed line. As shown in FIGS. 3A, 3B and 3C, a camera 302 for capturing an image of reflections of light pulses from the user's eye, is arranged substantially along the gaze direction of the user's eye. The camera 302 comprises an objective lens 302A and a chip 302B having a plurality of photo-sensitive elements (not shown) arranged therein.

Figures 3D, 3E:
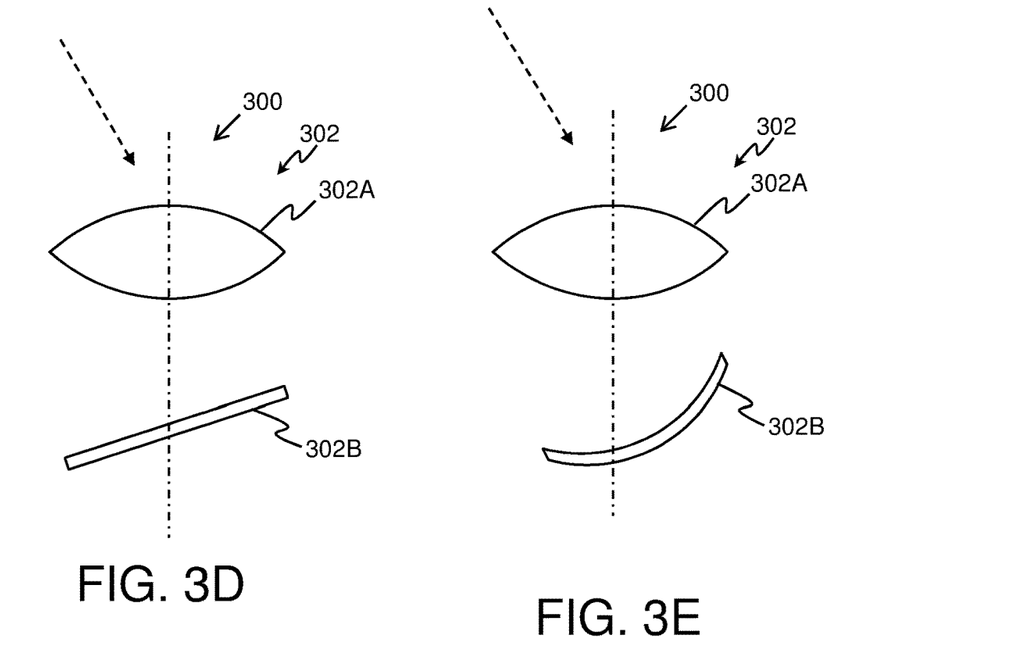
FIGS. 3D, 3E, 3F and 3G illustrate exemplary implementations of a side imaging arrangement of a gaze-tracking system, in accordance with different embodiments of the present disclosure.

In FIGS. 3A and 3E, the chip 302B bulges inwards in a substantially-curved shape. In FIGS. 3B, 3C, 3D, 3F and 3G, the chip 302B has a substantially flat shape. Furthermore, in FIG. 3B, there is also shown a third optical element, depicted as a plano-concave field lens 304, that is arranged between the objective lens 302A and the chip 302B. In FIG. 3C, the gaze-tracking system 300 comprises an axicon lens 306, wherein the axicon lens 306 is arranged between the objective lens 302A and the chip 302B.

Figure 3F:
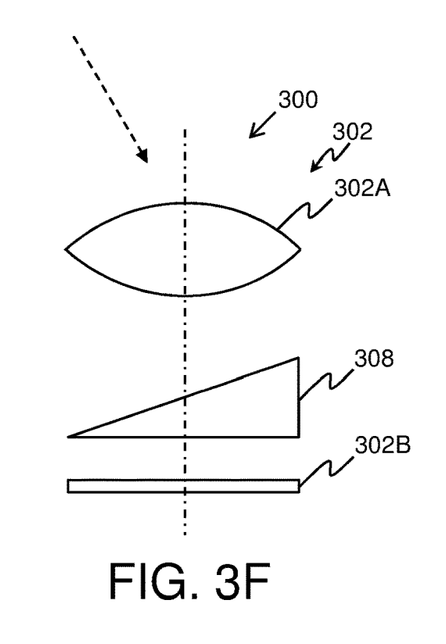
Figure 3G:
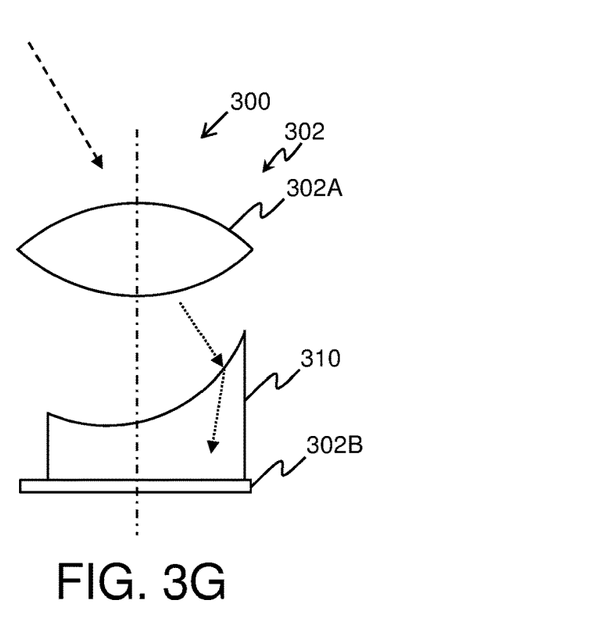

In FIGS. 3D, 3E, 3F and 3G, the camera 302 is arranged substantially away from the gaze direction of the user's eye. A camera optical axis of the camera 302 is depicted as the dashed-dot line. In FIGS. 3D and 3E, the chip 302B is tilted with respect to the camera optical axis. In FIG. 3F, the gaze-tracking system 300 includes a third optical element, depicted as a prism 308, that is arranged between the objective lens 302A and the chip 302B. The prism 308 allows for sharply focusing reflections of light pulses incident upon a focal plane (not shown) of the camera 302, at the chip 302B, even upon change in orientation of the objective lens 302A. Furthermore, the prism 308 also allows for implementing optical perspective correction that is required for the side imaging arrangement. In FIG. 3G, the gaze-tracking system 300 includes the third optical element, depicted as an asymmetrical plano-concave field lens 310, that is arranged between the objective lens 302A and the chip 302B. Furthermore, in FIG. 3G, an optical path of the reflections of the light pulses from the user's eye through the plano-concave field lens 310 is depicted using dotted lines.

Figure 4:
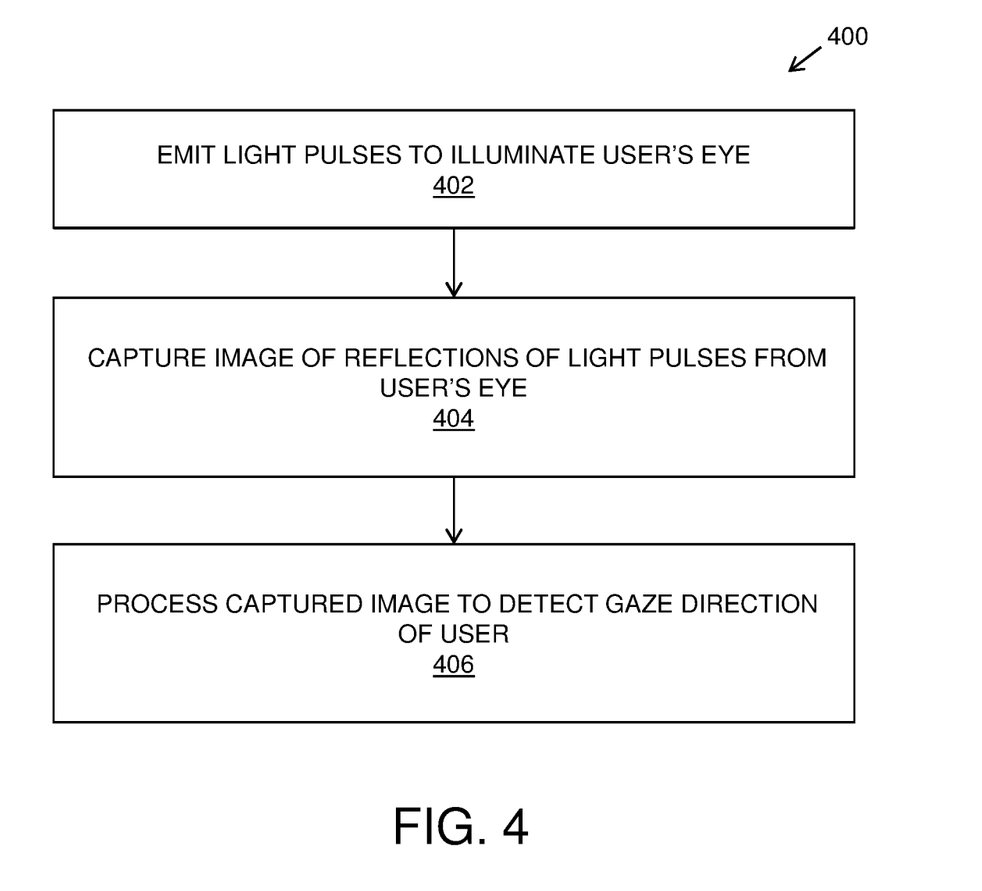
FIG. 4 illustrates steps of a method of tracking a user's gaze via a gaze-tracking system of a head-mounted display apparatus, in accordance with an embodiment of the present disclosure.

Referring to FIG. 4, illustrated are steps of a method 400 of tracking a user's gaze via a gaze-tracking system (for example, such as the gaze-tracking system 100 of FIG. 1) of a head-mounted display apparatus, in accordance with an embodiment of the present disclosure. At step 402, light pulses are emitted, via the plurality of illuminators, to illuminate a user's eye when the head-mounted display apparatus is worn by the user. At step 404, an image of reflections of the light pulses from the user's eye is captured, via the at least one camera. The image is representative of a position of the reflections on an image plane of the at least one camera, the at least one camera comprising a plurality of photo-sensitive elements arranged into at least one chip, wherein a first surface of the at least one chip bulges inwards in a substantially-curved shape, such that a focal plane of photo-sensitive elements positioned proximally to edges of the at least one chip is farther away than a focal plane of photo-sensitive elements positioned substantially at a center portion of the at least one chip, the first surface facing the user's eye when the head-mounted display apparatus is worn by the user. At step 406, the captured image is processed to detect a gaze direction of the user.

The steps 402 to 406 are only illustrative and other alternatives can also be provided where one or more steps are added, one or more steps are removed, or one or more steps are provided in a different sequence without departing from the scope of the claims herein.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

The invention claimed is:

1. A gaze-tracking system for use in a head-mounted display apparatus, the gaze-tracking system comprising:
   a plurality of illuminators for emitting light pulses to illuminate a user's eye when the head-mounted display apparatus is worn by the user;
   at least one camera for capturing an image of reflections of the light pulses from the user's eye, the image being representative of a position of the reflections on an image plane of the at least one camera, the at least one camera comprising a plurality of photo-sensitive elements arranged into at least one chip, wherein a first surface of the at least one chip bulges inwards in a substantially-curved shape, such that a focal plane of photo-sensitive elements positioned proximally to edges of the at least one chip is farther away than a focal plane of photo-sensitive elements positioned substantially at a center portion of the at least one chip, the first surface facing the user's eye when the head-mounted display apparatus is worn by the user; and
   a processor coupled in communication with the plurality of illuminators and the at least one camera, wherein the processor is configured to control operations of the plurality of illuminators and the at least one camera, and to process the captured image to detect a gaze direction of the user.

2. The gaze-tracking system of claim 1, wherein the plurality of illuminators comprise at least a first illuminator and a second illuminator that are to be arranged in a manner that light pulses emitted by the first illuminator are incident upon a first portion of the user's eye, and light pulses emitted by the second illuminator are incident upon a second portion of the user's eye, the first portion of the user's eye being farther away from the at least one camera than the second portion of the user's eye, wherein the first and second portions lie within a depth of field of a focal plane of the at least one camera.

3. The gaze-tracking system of claim 1, further comprising at least one optical element positioned on an optical path of the reflections, wherein optical characteristics and/or an arrangement of the at least one optical element are such that a shift in a given portion of the at least one chip along a camera optical axis by a micrometer leads to a shift in a focal plane of photo-sensitive elements positioned within the given portion of the at least one chip along the camera optical axis by a certain distance, the certain distance lying within a range of 1 mm to 10 mm.

4. The gaze-tracking system of claim 1, wherein the at least one chip is attached to a substantially-concave surface.

5. The gaze-tracking system of claim 1, wherein the light pulses emitted by the plurality of illuminators have an infra-red wavelength or a near infra-red wavelength.

6. The gaze-tracking system of claim 1, wherein the at least one camera comprises at least one optical filter for blocking unwanted parts of light spectrum, the at least one optical filter being positioned on an optical path of the reflections.

7. A method of tracking a user's gaze, via a gaze-tracking system of a head-mounted display apparatus, the gaze-tracking system comprising a plurality of illuminators and at least one camera, the method comprising:

emitting light pulses, via the plurality of illuminators, to illuminate a user's eye when the head-mounted display apparatus is worn by the user;

capturing an image of reflections of the light pulses from the user's eye, via the at least one camera, the image being representative of a position of the reflections on an image plane of the at least one camera, the at least one camera comprising a plurality of photo-sensitive elements arranged into at least one chip, wherein a first surface of the at least one chip bulges inwards in a substantially-curved shape, such that a focal plane of photo-sensitive elements positioned proximally to edges of the at least one chip is farther away than a focal plane of photo-sensitive elements positioned substantially at a center portion of the at least one chip, the first surface facing the user's eye when the head-mounted display apparatus is worn by the user; and processing the captured image to detect a gaze direction of the user.

8. The method of claim 7, wherein the plurality of illuminators comprise at least a first illuminator and a second illuminator, and the method further comprises arranging the first illuminator and the second illuminator in a manner that light pulses emitted by the first illuminator are incident upon a first portion of the user's eye, and light pulses emitted by the second illuminator are incident upon a second portion of the user's eye, the first portion of the user's eye being farther away from the at least one camera than the second portion of the user's eye, wherein the first and second portions lie within a depth of field of a focal plane of the at least one camera.

9. The method of claim 7, wherein the gaze-tracking system further comprises at least one optical element positioned on an optical path of the reflections, wherein optical characteristics and/or an arrangement of the at least one optical element are such that a shift in a given portion of the at least one chip along a camera optical axis by a micrometer leads to a shift in a focal plane of photo-sensitive elements positioned within the given portion of the at least one chip along the camera optical axis by a certain distance, the certain distance lying within a range of 1 mm to 10 mm.

10. The method of claim 7, wherein the at least one chip is attached to a substantially-concave surface.

11. The method of claim 7, wherein the light pulses emitted by the plurality of illuminators have an infra-red wavelength or a near infra-red wavelength.

12. The method of claim 7, wherein the at least one camera comprises at least one optical filter for blocking unwanted parts of light spectrum, the at least one optical filter being positioned on an optical path of the reflections.

* * * * *